United States Patent
Patel et al.

(10) Patent No.: US 10,568,520 B2
(45) Date of Patent: Feb. 25, 2020

(54) MICRO-MOLDED ANAMORPHIC REFLECTOR LENS FOR IMAGE GUIDED THERAPEUTIC/DIAGNOSTIC CATHETERS

(71) Applicant: AVINGER, INC., Redwood City, CA (US)

(72) Inventors: Himanshu N. Patel, San Jose, CA (US); Manish Kankaria, Fremont, CA (US); Kin F. Chan, Los Gatos, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 15/741,928

(22) PCT Filed: Jul. 13, 2016

(86) PCT No.: PCT/US2016/042152
§ 371 (c)(1),
(2) Date: Jan. 4, 2018

(87) PCT Pub. No.: WO2017/011587
PCT Pub. Date: Jan. 19, 2017

(65) Prior Publication Data
US 2018/0192880 A1 Jul. 12, 2018

Related U.S. Application Data

(60) Provisional application No. 62/191,986, filed on Jul. 13, 2015, provisional application No. 62/191,956, filed on Jul. 13, 2015.

(51) Int. Cl.
*A61B 5/00* (2006.01)
*A61B 90/00* (2016.01)
*G01B 9/02* (2006.01)

(52) U.S. Cl.
CPC .......... *A61B 5/0084* (2013.01); *A61B 5/0066* (2013.01); *G01B 9/02091* (2013.01);
(Continued)

(58) Field of Classification Search
CPC . A61B 5/0066; A61B 5/0084; A61B 5/02007; A61B 2090/3614;
(Continued)

(56) References Cited

U.S. PATENT DOCUMENTS

| 3,908,637 A | 9/1975 | Doroshow |
| 4,178,935 A | 12/1979 | Gekhaman et al. |

(Continued)

FOREIGN PATENT DOCUMENTS

| CN | 1875242 A | 12/2006 |
| CN | 1947652 A | 4/2007 |

(Continued)

OTHER PUBLICATIONS

Aziz et al.; Chronic total occlusions—a stiff challege requiring a major breakthrough: is there light at the end of the tunnel?; Heart; vol. 91; suppl. III; pp. 42-48; Jun. 2005.
(Continued)

*Primary Examiner* — Michael A Lyons
(74) *Attorney, Agent, or Firm* — Shay Glenn LLP

(57) ABSTRACT

A catheter system for optical coherence tomography includes an elongate catheter body, an optical fiber in the elongate catheter body, and an anamorphic lens assembly coupled with a distal end of the optical fiber. The optical fiber and the lens assembly are together configured to provide a common path for optical radiation reflected from a target and from a reference interface between the distal end of the optical fiber and the lens assembly.

13 Claims, 14 Drawing Sheets

(52) U.S. Cl.
CPC ............... *A61B 2090/3614* (2016.02); *A61B 2562/0233* (2013.01)

(58) Field of Classification Search
CPC ........ A61B 2562/0233; G01B 9/02091; G02B 5/04; G02B 17/06; G02B 17/0688; G02B 27/0911; G02B 27/0983
See application file for complete search history.

(56) References Cited

U.S. PATENT DOCUMENTS

| | | |
|---|---|---|
| 4,487,206 A | 12/1984 | Aagard |
| 4,527,553 A | 7/1985 | Upsher |
| 4,552,554 A | 11/1985 | Gould et al. |
| 4,611,600 A | 9/1986 | Cohen |
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,691,708 A | 9/1987 | Kane |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |

(56) References Cited

U.S. PATENT DOCUMENTS

| | | |
|---|---|---|
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |

(56) References Cited

U.S. PATENT DOCUMENTS

| | | |
|---|---|---|
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0021926 A1 | 1/2010 | Noordin |
| 2010/0049225 A1 | 2/2010 | To et al. |
| 2010/0080016 A1 | 4/2010 | Fukui et al. |
| 2010/0125253 A1 | 5/2010 | Olson et al. |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0238869 A1 | 9/2012 | Schmitt et al. |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0296695 A1 | 11/2013 | Spencer et al. |
| 2013/0317519 A1 | 11/2013 | Romo et al. |
| 2014/0005534 A1 | 1/2014 | He et al. |
| 2014/0128893 A1 | 5/2014 | Guggenheimer et al. |
| 2014/0187949 A1 | 7/2014 | Zhao et al. |
| 2014/0222047 A1 | 8/2014 | Vreeman |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0141816 A1 | 5/2015 | Gupta et al. |
| 2015/0146211 A1 | 5/2015 | Bhagavatula et al. |

(56) References Cited

U.S. PATENT DOCUMENTS

| | | |
|---|---|---|
| 2015/0164530 A1 | 6/2015 | Carver et al. |
| 2015/0208922 A1 | 7/2015 | Simpson et al. |
| 2015/0320975 A1 | 11/2015 | Simpson et al. |
| 2016/0008025 A1 | 1/2016 | Gupta et al. |
| 2016/0038030 A1 | 2/2016 | Smith et al. |
| 2016/0135832 A1 | 5/2016 | Simpson et al. |
| 2016/0144155 A1 | 5/2016 | Simpson et al. |
| 2016/0262791 A1 | 9/2016 | Patel et al. |
| 2016/0262839 A1 | 9/2016 | Spencer et al. |
| 2016/0338582 A1 | 11/2016 | Tachibana et al. |
| 2017/0065293 A1 | 3/2017 | Rosenthal et al. |
| 2017/0065295 A1 | 3/2017 | Patel et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0042520 A1 | 2/2018 | Patel et al. |
| 2018/0049700 A1 | 2/2018 | Black et al. |
| 2018/0364024 A1* | 12/2018 | Baca .................. G01B 9/0205 |

FOREIGN PATENT DOCUMENTS

| | | |
|---|---|---|
| CN | 101601581 A | 12/2009 |
| CN | 103027727 A | 4/2013 |
| DE | 202006018883 U1 | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2353526 B1 | 9/2013 |
| EP | 2942028 A1 | 11/2015 |
| JP | S62-275425 A | 11/1987 |
| JP | 03502060 A | 2/1990 |
| JP | 05103763 A | 4/1993 |
| JP | 06027343 A | 2/1994 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 A | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012533353 A | 12/2012 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/166332 A1 | 12/2012 |
| WO | WO2013/033490 A1 | 3/2013 |
| WO | WO2013/056262 A1 | 4/2013 |
| WO | WO2014/093148 A2 | 6/2014 |
| WO | WO2015/074018 A1 | 5/2015 |
| WO | WO2015/120146 A1 | 8/2015 |
| WO | WO2017/007853 A1 | 1/2017 |
| WO | WO2017/132247 A1 | 8/2017 |

OTHER PUBLICATIONS

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Patel et al.; U.S. Appl. No. 15/324,325 entitled "High speed chronic total occulusion crossing devices," filed Jan. 6, 2017.

Smith et al.; U.S. Appl. No. 15/854,579 entitled "Chronic total occusion crossing devices with imaging," filed Dec. 26, 2017.

Zung et al.; US. Appl. No. 15/741,773 entitled "Self-alignment mechanism for imaging cather and drive assembly," filed Jan. 4, 2018.

Simpson et al.; U.S. Appl. No. 16/194,183 entitled "Identification of elastic lamina to guide interventional therapy," filed Nov. 16, 2018.

Fernandez et al., U.S. Appl. No. 16/305,136 entitled "Catheter device with detachable distal end," filed Nov. 28, 2018.

(56) References Cited

OTHER PUBLICATIONS

Patel et al., U.S. Appl. No. 16/310,470 entitled "Atherectomy catheter with shapeable distal tip," filed Dec. 17, 2019.
Patel et al.; U.S. Appl. No. 15/922,058 entitled "Catheter system and method for boring through blocked vascular passages," filed Mar. 15, 2018.
Newhauser et al.; U.S. Appl. No. 15/954,407 entitled "Occlusion-crossing devices," filed Apr. 16, 2018.
Christensen; U.S. Appl. No. 16/069,545 entitled "OCT imaging catheter with lag correction," filed Jul. 12, 2018.
Rosenthal et al.; U.S. Appl. No. 16/105,743 entitled "Atherectomy catheter with laterally-displaceable tip," filed Aug. 20, 2018.
Patel et al.; U.S. Appl. No. 16/148,246 entitled "Atherectomy catheter with serrated cutter," filed Oct. 1, 2018.
Choma et al.; Sensitivity advantage of swept source and fourier domain optical coherence tomography; Optics Express; 11(18); pp. 2183-2189; Sep. 8, 2003.
De Boer et al.; Improved signal-to-noise ratio in spectral-domain compared with time-domain optical coherence tomography; Optics Letters; 28(21); pp. 2067-2069; Nov. 2003.
Leitgeb et al.; Performance of fourier domain vs time domain optical coherence tomography; Optics Express; 11(8); pp. 889-894; Apr. 21, 2003.
Rollins et al.; Optimal interferometer designs for optical coherence tomography; Optics Letters; 24(21); pp. 1484-1486; Nov. 1999.
Tachibana et al.; U.S. Appl. No. 16/372,112 entitled "Atherectomy catheter drive assemblies," filed Apr. 1, 2019.
Radjabi et al.; U.S. Appl. No. 16/347,840 entitled "Methods, systems and apparatuses for displaying real-time catheter position," filed May 7, 2019.

\* cited by examiner

MICRO-MOLDED ANAMORPHIC REFLECTOR LENS FOR IMAGE GUIDED THERAPEUTIC/DIAGNOSTIC CATHETERS

CROSS REFERENCE TO RELATED APPLICATIONS

This application claims priority to U.S. Provisional Patent Application No. 62/191,956, filed Jul. 13, 2015, titled "MICRO-MOLDED ANAMORPHIC REFLECTOR LENS FOR IMAGE GUIDED THERAPEUTIC/DIAGNOSTIC CATHETERS," and U.S. Provisional Patent Application No. 62/191,986, filed Jul. 13, 2015 and titled "CARBON DIOXIDE CARTRIDGE FOR BALLOON CATHETER," each of which is incorporated by reference in its entirety.

This application may be related to U.S. patent application Ser. No. 14/400,140, filed on Nov. 10, 2014 (titled "OPTICAL COHERENCE TOMOGRAPHY WITH GRADED INDEX FIBER FOR BIOLOGICAL IMAGING"), which is incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are imaging devices and systems for use in biological probes. In particular, described herein are catheter-based imaging systems using Optical Coherence Tomography (OCT) having a molded lens adapted to minimize parasitic back-reflections and provide superior distance imaging and beam diameter characteristics.

BACKGROUND

A number of vascular diseases, such as coronary artery disease and peripheral vascular disease, are caused by the build-up of atherosclerotic deposits (plaque) in the arteries, which limit blood flow to the tissues that are supplied by that particular artery. Disorders caused by occluded body vessels, including coronary artery disease (CAD) and peripheral artery disease (PAD), may be debilitating and life-threatening. Chronic Total Occlusion (CTO) can result in limb gangrene, requiring amputation, and may lead to other complications and eventually death. Increasingly, treatment of such blockages may include interventional procedures in which a guidewire is inserted through a catheter into the diseased artery and threaded to the blocked region. There the blockage may be either expanded into a more open position, for example, by pressure from an inflated catheter balloon (e.g., balloon angioplasty) and/or the blocked region may be held open by a stent. Treatment of such blockages can also include using a catheter to surgically remove the plaque from the inside of the artery (e.g., an atherectomy).

There is medical interest in equipping catheters with sensors that can help direct the catheter for atherectomy, occlusion-crossing, and/or other surgical procedures. For example, it would be useful to have sensors that can give the surgeon immediate visual feedback as to whether a particular tissue is diseased and/or how far away the cutting portion of a catheter is from the boundary of a particular blood vessel layer to minimize the risk of accidental damage.

Conventional radiological imaging methods and ultrasound imaging systems have been attempted for such surgical procedures. However, neither ultrasound nor radiological imaging methods have enough resolution to help guide the operation of the catheter through small dimensions. Moreover, standard radiological techniques cannot easily discriminate between healthy tissue and diseased tissue unless the tissue has become heavily calcified. Further, the components of an ultrasound system are generally too large to implement on a small scale, such as with a system configured to be used within blood vessels.

Optical Coherence Tomography (OCT) has been proposed as one technique that may be particularly helpful for imaging regions of tissue, including within a body lumen such as a blood vessel. At a basic level, OCT relies on the fact that light traveling from a source and scattering from more distant objects takes longer to travel back than light scattering from nearby objects. Due to the wave nature of light, very small timing differences caused by light signals traveling different distances on the micron scale can cause constructive or destructive interference with reference light signals. OCT systems measure the resulting interference to obtain an image of the target. A typical OCT system requires one or more interferometers to distinguish the signal from the applied light. In addition, most known OCT systems, when applied to catheters, include a fiber that is rotated (often at high rates) within the catheter in order to scan the lumen and a second, large reference arm.

A typical OCT device includes a target arm and a reference arm to generate a reference signal. In order to provide the interference reference signal, the OCT device will split an illuminating light signal from the source in two equal or unequal parts, send part of the illuminating light to the target of interest through one target optical "target arm" and send the other part of the illuminating light down a separate reference arm. Light from the separate reference arm reflects off of a mirror, and then returns and interferes with the scattered light that is returning from the target optical arm after bouncing off of the target. In a traditional OCT device, the reference arm length is engineered to be exactly the same length as the target arm so that the interference effect is maximized. The resulting interference between the two beams creates interference that can be measured to extract depth information related to the target. Using this depth information, an image of the object can be generated. A typical OCT device can further include a focusing lens in the target arm, such as a graded index (GRIN) lens, configured to focus the light coming out of the optical fiber into the tissue.

These traditional OCT systems, however, are large and cumbersome due to the required reference arm and are therefore generally ineffective for use in a medical catheter, particularly for use with a low cost and disposable catheter. Using a common path OCT system, i.e., a system without a separate reference arm, is one way to eliminate the cost and size of such an imaging catheter. There are several challenges, however, associated with developing a catheter having common path OCT. For example, a common path OCT system requires that the reference reflection be formed within the same optical conduit as the target reflection. This reference reflection must be finely tuned to avoid noise in the system, requiring that the path from the light source to the reflection interface be free of unnecessary components, such as focusing elements that could interfere with the reference reflection. Further, the common path system must have components that are small enough to fit inside of a single small catheter, making it difficult to include additional components. Finally, for common path OCT, it is desirable to have the reference reflection as close to the tissue as possible to maintain the imaging range within the coherence length of the source and avoid data processing burden, as data processed for the distance between the reference and the start of the imaging is not useful. Accordingly, a common path OCT system that solves some of these problems is desired.

The distal imaging tip of a common-path OCT catheter should perform two main functions: (1) direct the beam towards the imaging object and (2) focus the beam on the imaging object for improved image quality. In addition, for common path OCT, the geometry and properties of the distal imaging assembly should be such that it introduces only one primary source of back-reflection (reference reflection) and avoid any other parasitic reflection which could causes artifacts in the images.

One way to address these needs that has been proposed (see, e.g., US-2015-0099984) which uses a common-path OCT system with a graded index (GRIN) fiber attached to the distal tip of a single mode optical fiber in the catheter so as to act as a lens for focusing light. Unfortunately, this solution has proven problematic. For example, the addition of any lens (e.g., a graded index (GRIN) lens) is difficult and results in potential failure modes. FIG. 1 illustrates a prior-art device 100, such as a catheter, having housing 109 holding a graded index (GRIN) fiber 103 at the end of an optical fiber 110, forming a grins lens assembly. In this example, deflection and focusing of the beam is accomplished using two separate components. First, a mirror 101 is mounted at 45 degrees to the axis of the optical fiber 110 to deflect the beam perpendicular to axis of the catheter, as shown by beam 113. Second, the graded index fiber 103 is spliced to the optical fiber 110, which is a single mode fiber (SMF) assembly, in order to focus the beam. The GRIN fiber 103 is spliced in front of the SMF fiber 110 and then cleaved to precise length and angle to meet the focusing and reference reflection requirements in conjunction with the epoxy 102 used to secure the GRIN fiber 103 at the distal tip. The precision splicing and cleaving requirements for this SMF-GRIN assembly makes it an expensive component for the device 100.

Further, the manufacturing processes required to make these SMF-GRIN assemblies, such as that in device 100, is often difficult and requires precision alignment. Moreover, in order to splice the GRIN fiber 103 in front of the SMF fiber 110, the SMF fiber must be stripped to certain length (see stripped section 105 in FIG. 1). Stripping of the fiber SMF fiber, especially polyimide fibers, typically renders a long fragile portion 132 of fiber. The total length of the fragile portion 132 of the SMF-GRIN assembly may be greater than 2.5 mm. This fragile portion 132 often must be encapsulated inside a solid hypo tube, to prevent the distal portion from breaking while subjected to stress/strain while imaging in tortuous anatomy. The presence of the long (e.g., >2.5 mm) hypo tube in the device 100 reduces the flexibility of the distal tip. Thus, when the device 100 is part of a catheter, such as an atherectomy catheter, this reduced flexibility can make it difficult to access the tortuous section of the anatomy.

Moreover, focusing length may be sacrificed by using a GRIN fiber 103 and separate mirror 101. The focusing capability of the GRIN fiber 103 is a function of the diameter of the fiber. Using 125 micron GRIN fiber 103, to match the diameter of the SMF 110, the focus point is limited to 1-1.5 mm from the tip of the fiber. In imaging catheters where the fiber is deployed in the middle of the catheter, significant portion of the Rayleigh range of the beam could be lying inside the catheter. This reduces the imaging depth within which the imaging catheter is able to maintain high resolution.

Described herein are apparatuses, including tip assemblies for OCT (common path) imaging systems, and methods of making an using them, that may address the issues raised above.

SUMMARY OF THE DISCLOSURE

In general, described herein are OCT apparatuses (including devices and systems) that include a lens assembly that is, or is capable of being, positioned at distal tip of an optical fiber to provide common-path OCT imaging. The lens assembly is typically an anamorphic lens assembly.

In some embodiments, the anamorphic lens assembly has a lens body, and a first surface coupled to the optical fiber through which light from the optical fiber may pass into the lens body so that it can be reflected from a second, reflective, surface at an angle, to direct light out of the lens assembly and into a tissue (e.g., at a 45 degree angle). The second, reflective, surface may have a compound radius so that the beam profile of the light beam from the optical fiber is made approximately circular as it exits the lens assembly (e.g., out of a third, flat, surface that is perpendicular to the direction of the beam) reflected from the second surface).

In other embodiments, the anamorphic lens assembly has a concave proximal surface that is reflective and includes a compound surface to reflect light therefrom.

The lens assemblies described herein may be used as part of a catheter capable of OCT imaging. For example, a catheter for optical coherence tomography (OCT) may include: an elongate catheter body extending distally to proximally, an optical fiber in the elongate catheter body, and a lens assembly optically coupled with a distal end of the optical fiber, the lens assembly, wherein the optical fiber and the lens assembly are together configured to provide a common path for optical radiation reflected from a target and from a reference interface between the distal end of the optical fiber and the first surface.

As mentioned, the lens assembly may be an anamorphic lens assembly, refractive or reflective, e.g., having non-uniform or different magnifications or radii of curvatures along the two axes perpendicular to each other (e.g., the axis perpendicular to the path of light traveling through the lens body). In some variations, the anamorphic lens may refer specifically to the compound radii of curvature of the mirror portion. In other variations, the anamorphic lens may refer to a mirror having continuously changing or different radii of curvature between the two perpendicular axes.

In any of the variations described herein, the lens assembly (e.g., the first surface of the lens assembly) may be connected to the distal end of the optical fiber by a layer of epoxy.

In general, some embodiments, the first surface (the surface immediately opposite the distal end of the optical fiber) may be at an angle relative to the distal end (out of which the light passes) of between about 2 degrees and 40 degrees relative to the distal end of the optical fiber, e.g., the angle may be between about 5 degrees and 13 degrees, between about 2 degrees and 20 degrees, between 6 degrees and 10 degrees, about 8 degrees, etc.). Further, the second (reflective, or mirrored) surface is angled relative to the distal end of the optical fiber, so that light traveling to/from the distal end of the optical fiber, after passing the first surface of the lens body, is reflected by the second surface and directed laterally out of the lens. For example, the second surface may be at an angle of between about 10 degrees and about 60 degrees (e.g., 20 degrees and 50 degrees, 30 degrees and 50 degrees, 40 degrees and 50 degrees, about 45 degrees, etc.) relative to the distal end of the optical fiber.

In some embodiments, the reflective proximal surface can be angled relative to the distal end of the optical fiber, so that light traveling to/from the distal end of the optical fiber and impinging on the proximal surface is reflected and directed laterally out of the lens. For example, the proximal surface may be at an angle of between about 10 degrees and about 60 degrees (e.g., 20 degrees and 50 degrees, 30 degrees and 50 degrees, 40 degrees and 50 degrees, about 45 degrees, etc.) relative to the distal end of the optical fiber The reflective second surface may be formed by coating (and/or attaching) a reflective material to the outer face of the second surface. The reflective material coating the second surface may be coated at a thickness that is configured to reflect more than 70% (e.g., more than 75%, more than 80%, more than 85%, more than 90%, more than 95%, etc.) of light. Any appropriate reflective material may be used. For example, the reflective material may comprise gold, silver, platinum, etc.

In general, the reflective surfaces may comprise a compound radius, e.g., a compound radius having a different radius in an x and a y axis. The compound radius may be configured so that light (e.g., a beam of light) reflecting off of the second surface has a beam profile that is more circular when it exits the lens body than when it entered the lens body.

The lens (e.g., the lens body) may be formed of any material, particularly materials that may be molded. For example, the lens body may be formed of a polycarbonate material having a refractive index that is mismatched relative to the refractive index of the optical fiber. Thus, for example, a secondary reflection of optical radiation from an interface between the optical fiber and the lens assembly may be less than −60 dB. Further, the reference interface may provide a reference reflection of between about −28 and about −42 dB.

Any of the lens apparatuses, and/or any of the catheters including such lens apparatuses, described herein may be configured as a system including a light source and receiving electronics which may include a processor for generating OCT images. For example, a system for optical coherence tomography (OCT) may include: a source of optical radiation, an optical fiber extending distally to proximally, and a lens assembly optically coupled with a distal end of the optical fiber, wherein the optical fiber and the lens assembly are together configured to provide a common path for optical radiation reflected from a reference interface between the distal end of the optical fiber and the first surface, and from a target. The system can further include receiving electronics configured to receive the optical radiation reflected from the reference interface and the target and a processor to generate an image of the target based upon the optical radiation received by the receiving electronics.

Also described herein are method of takin OCT images including passing light from an optical fiber and into or off of a lens apparatus as described herein, The method can include creating minimal (e.g., less than −55 dB) secondary reflection results. The method may also include reflecting the light (beam) from the reflective surface at an angle of between about 30 degrees and 60 degrees (e.g., approximately 45 degrees) so that it projects laterally out of the device and into the tissue, then collecting light returning from the tissue and passing it back through the lens body and into the fiber optic, where it can be collected and processed (e.g., using a receiver and/or processor) to form an optical coherence tomographic image.

In general, in one embodiment, a catheter system for optical coherence tomography (OCT) includes an elongate catheter body extending distally to proximally, an optical fiber in the elongate catheter body, and a lens assembly optically coupled with a distal end of the optical fiber. The lens assembly includes a lens body having a first surface that is opposite from and at an angle relative to the distal end of the optical fiber and a second surface distal to the first surface. The second surface is coated with a reflective material so that light passing from the distal end of the optical fiber, through the first surface, and into the lens body reflects off of the second surface and out of the lens body. The optical fiber and the lens assembly are together configured to provide a common path for optical radiation reflected from a target and from a reference interface between the distal end of the optical fiber and the first surface.

In general, in one embodiment, a catheter system for optical coherence tomography (OCT) includes an elongate catheter body extending distally to proximally, an optical fiber in the elongate catheter body, and a lens assembly optically coupled with a distal end of the optical fiber. The lens assembly includes a lens body having a first surface that is opposite from and at an angle relative to the distal end of the optical fiber and a second surface distal to the first surface. The second surface has a compound radius having a first radius along a first axis that is different from a second radius along a second axis. That light passing from the distal end of the optical fiber, through the first surface, and into the lens body reflects off of the second surface and out of the lens body. The optical fiber and the lens assembly are together configured to provide a common path for optical radiation reflected from a target and from a reference interface between the distal end of the optical fiber and the first surface.

In general, in one embodiment, a catheter system for optical coherence tomography (OCT) includes an elongate catheter body extending distally to proximally, an optical fiber in the elongate catheter body, and a lens assembly having a first refractive index optically coupled with a distal end of the optical fiber by an interface medium. The interface medium has a second refractive index. The first refractive index and the second refractive index differ by 0.02 or less. The lens assembly includes a lens body having a first surface that is opposite from the distal end of the optical fiber and a second surface distal to the first surface. Light passing from the distal end of the optical fiber through the first surface and into the lens body reflects off of the second surface and out of the lens body. The optical fiber and the lens assembly are together configured to provide a common path for optical radiation reflected from a target and from a reference interface between the distal end of the optical fiber and the interface medium.

These and other embodiments can include one or more of the following features. The lens assembly can be an anamorphic lens assembly. The catheter system can further include an interface medium connecting the distal end of the optical fiber and the first surface. The interface medium can be an epoxy. The lens assembly can have a first refractive index and the interface medium can have a second refractive index, wherein the first refractive index and the second refractive index can differ by 0.02 or less. The first surface can be at an angle of 8 degrees or more relative to the distal end of the optical fiber. A tangent of the second surface can be at an angle of between about 40 degrees and 50 degrees relative to a longitudinal axis of the fiber. The catheter system can further include a reflective coating on the second surface. The reflective coating can have a thickness that is configured to reflect more than 80% of light. The reflective coating can be gold. The reflective material can be dielectric. The second surface can include a compound radius. The second surface can include a compound radius having a first radius along a first axis that is different than a second radius along a second axis. The lens body can include a polycarbonate material. A secondary reflection of optical radiation from an interface between the optical fiber and the lens assembly can be less than −60 dB. The reference interface can provide a reference reflection of between −28 and −42 dB. The second surface can be concave relative to the light passing from the distal end of the optical fiber. An exit surface of the lens assembly can be angled by 8 degrees or more relative to a central longitudinal axis of the optical fiber. The reflective coating can have an optical density of greater than or equal to 3.0. A radius of curvature of the second surface can be between 0.2 mm and 1.5 mm. The catheter system can further include a source of optical radiation configured to provide the light, and a reflective coating on the second surface can have a thickness of at least $\frac{1}{6}$ of an excitation wavelength of the source of optical radiation. The catheter system can further include a source of optical radiation, receiving electronics configured to receive optical radiation reflected from the reference interface and the target, and a processor to generate an image of the target based upon the optical radiation received by the receiving electronics.

In general, in one embodiment, a catheter for optical coherence tomography (OCT) includes an elongate catheter body extending distally to proximally, an optical fiber in the elongate catheter body, and a lens assembly optically coupled with a distal end of the optical fiber by an interface medium. The lens assembly includes a lens body having a concave proximal surface that is opposite from and at an angle relative to the distal end of the optical fiber. The proximal surface has a compound radius having first radius along a first axis that is different from a second radius along a second axis. The proximal surface includes a reflective material configured to so that at least 90% light passing from the distal end of the optical fiber through the lens assembly reflects off of the proximal surface. The optical fiber and the lens assembly are together configured to provide a common path for optical radiation reflected from a target and from a reference interface between the distal end of the optical fiber and the proximal surface.

This and other embodiments can include one or more of the following features. The interface medium can be an epoxy. A tangent of the proximal surface can be at an angle of between about 40 degrees and 50 degrees relative to a longitudinal axis of the fiber. The reflective material can include a reflective coating on the proximal surface. The reflective coating can be gold. The reflective material can be dielectric. The lens body can include a polycarbonate material. A secondary reflection of optical radiation from an interface between the optical fiber and the lens assembly can be less than −60 dB. The reference interface can provide a reference reflection of between −28 and −42 dB. The reflective coating can have an optical density of greater than 3.0. A radius of curvature of the proximal surface can be between 0.2 mm and 1.5 mm. The catheter system can further include a source of optical radiation configured to provide the light, wherein a reflective coating on the proximal surface can have a thickness of at least $\frac{1}{6}$ of an excitation wavelength of the source of optical radiation. The catheter system can further include a source of optical radiation, receiving electronics configured to receive optical radiation reflected from the reference interface and the target, and a processor to generate an image of the target based upon the optical radiation received by the receiving electronics.

In general, in one embodiment, a catheter for optical coherence tomography (OCT) includes an elongate catheter body extending distally to proximally, an optical fiber in the elongate catheter body, and a lens assembly optically coupled with a distal end of the optical fiber. The lens assembly includes a lens body having a first surface that is opposite from and at an angle relative to the distal end of the optical fiber and a second surface distal to the first surface. The second surface is uncoated such that light passing from the distal end of the optical fiber, through the first surface, and into the lens body reflects off of the second surface by total internal reflection and out of the lens body. The optical fiber and the lens assembly are together configured to provide a common path for optical radiation reflected from a target and from a reference interface between the distal end of the optical fiber and the first surface.

In general, in one embodiment, a catheter for optical coherence tomography (OCT) includes an elongate catheter body extending distally to proximally, an optical fiber in the elongate catheter body, and a lens assembly optically coupled with a distal end of the optical fiber by an interface medium. The lens assembly includes a lens body having a concave proximal surface that is opposite from and at an angle relative to the distal end of the optical fiber. The proximal surface has a compound radius having first radius along a first axis that is different from a second radius along a second axis. The proximal surface is uncoated such that light passing from the distal end of the optical fiber, through the first surface, and into the lens body reflects off of the second surface by total internal reflection and out of the lens body. The optical fiber and the lens assembly are together configured to provide a common path for optical radiation reflected from a target and from a reference interface between the distal end of the optical fiber and the proximal surface.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A shows the proximal surface while FIG. 3B shows the distal surface.

DETAILED DESCRIPTION

Described herein are lens assemblies for use with an imaging device. Any of the lens assemblies described herein may be anamorphic lens assemblies (i.e., lens assemblies that are circularly nonsymmetric and have or produce unequal magnifications along two different axes, i.e., two different axes that are perpendicular to one another). The anamorphic lens, for example, can include two different radii along two different axes. The lens assemblies described herein may be used as part of any optical coherence tomography (OCT) device, and particularly as part of a common path OCT device, which may be included as part of a catheter or other device. The lens assembly may be, for example, placed in and/or on a distal tip of a catheter to: (1) direct the beam towards the imaging object and (2) focus the beam on the imaging object for improved image quality.

The lens assemblies described herein may be formed, e.g., using a mold. Thus, any of the lens assemblies may also be referred to as "molds" or "mold assemblies." In some embodiments, the lens assemblies described herein may be made from polycarbonate material, such as Makrolon 2558. In some embodiments, the refractive index of the lens assembly can be close to the refractive index of the interface medium (e.g., epoxy) used to connect the lens assembly to the distal end of the imaging fiber optic.

Figure 2:
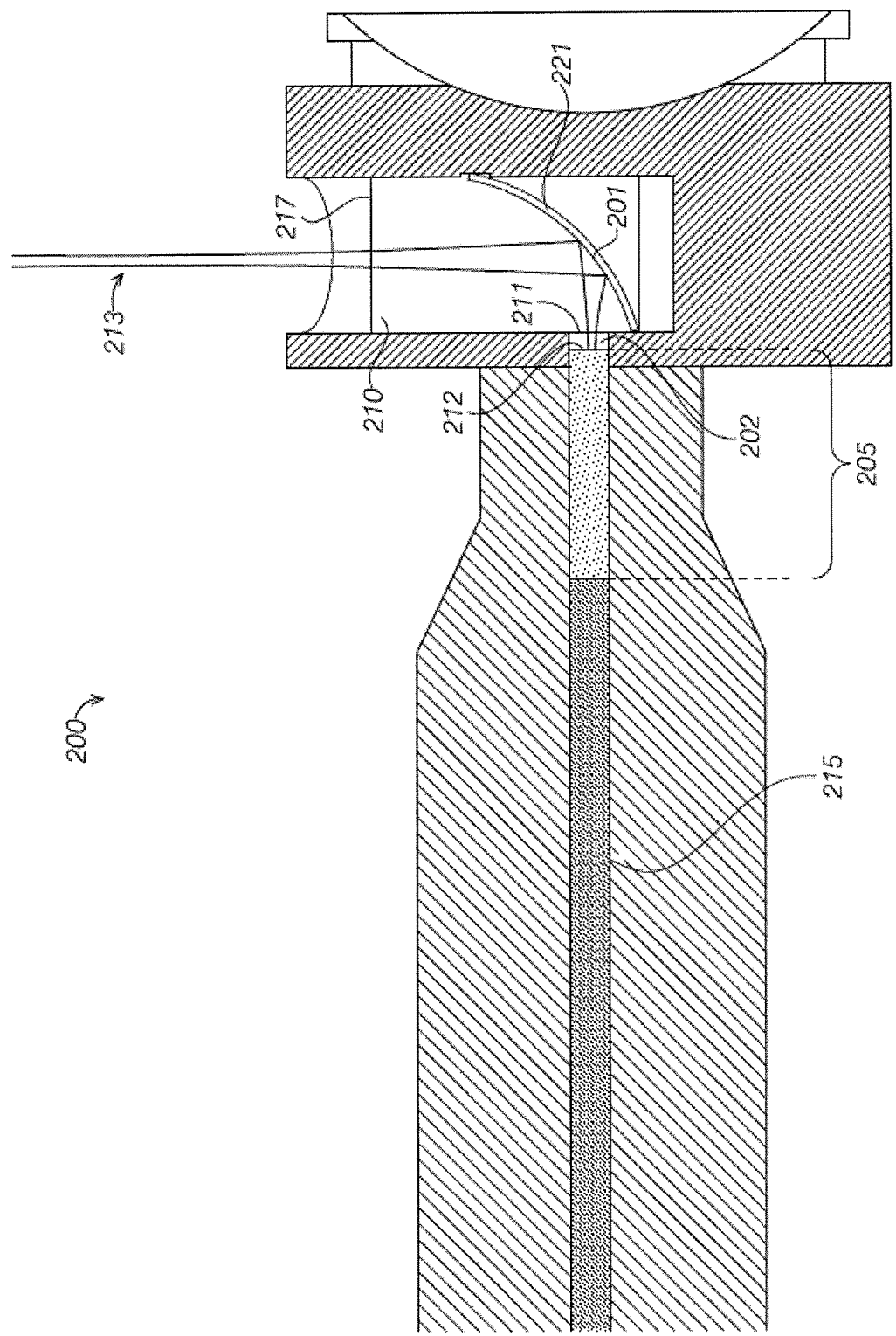
FIG. 2 is an example of a catheter including a lens assembly as described herein.

Referring to FIG. 2, an imaging device 200 can include an optical fiber 215, e.g., an SMF fiber, used as part of a common path OCT system. The device 200 further includes an anamorphic lens 210 attached to the distal end 212 of the optical fiber 215 with an interface medium 202 (e.g., an adhesive or epoxy). The index of refraction of the core of the optical fiber 215 and the index of refraction of the interface medium 202 can be mismatched as described in U.S. patent application Ser. No. 14/400,140, filed on Nov. 10, 2014 (titled "OPTICAL COHERENCE TOMOGRAPHY WITH GRADED INDEX FIBER FOR BIOLOGICAL IMAGING"), the entirety of which is incorporated by reference herein. Further, the index of refraction of the lens 210 and the interface medium 202 can be closely matched (e.g., within 0.02, such as within 0.01 or within 0.001).

The distal surface 221 of the lens can have a compound radius (e.g., a different radius along the x-axis than along the y-axis). Further, the outer portion of the distal surface 221 can be convex (i.e., such that light hits the concave inner portion). The distal surface 221 can have a radius of curvature, for example, of between 0.2 mm and 1.5 mm.

Further, the distal surface 221 can include a mirror 201 attached or coated thereon. Thus, the mirror 201 can include a coating and/or attached layer on the distal surface 221 of the lens 210. The mirror can have a thickness that is configured to reflect more than 70% (e.g., more than 75%, more than 80%, more than 85%, more than 90%, more than 95%, etc.) of light. In one example, the mirror or coating can have a thickness of greater than or equal to 100 nm, such as greater than or equal to 200 nm or greater than or equal to 250 nm in thickness. In some embodiments, the mirror or coating can have an optical density of 3.0 or greater, such as 3.5 or greater. Any appropriate reflective material may be used for the mirror or coating. For example, the reflective material may include gold, silver, or platinum. Further, the mirror 201 can be angled at approximately 45 degrees, where the angle is defined as the angle off the intersection of the fiber optical axis the second surface (i.e., the angle between the optical axis and the tangent to the compound second surface at the intersection with the second surface).

In this embodiment, the proximal surface 211 of the lens 210 can be oriented substantially parallel to the distal surface 212 of the optical fiber. Further, the outer surface 217 of the lens 210 can be substantially parallel to the axis of the fiber 215 (and therefore substantially perpendicular to the proximal surface 211 of the lens and the distal surface 212 of the optical fiber). In one embodiment, surfaces 211, 217 can be substantially flat. In another embodiment, the surfaces can be slightly curved with a radius of curvature of 0.1 inches or more.

In use, light from the light source can pass through the optical fiber 215. At the interface of the distal end 212 of the optical fiber and the interface medium 202, some of the light will be reflected back so as to create the reference reflection. The rest of the light can pass from the distal end 212 of the optical fiber through the interface medium 202, and through the proximal surface 211 of the lens. Because the indices of refraction of the fiber and the interface medium are closely matched, only a minimal amount (e.g., less than −55 dB) of light will be reflected back from the surface 211. The light can thus travel through the lens 210 and impinge on the mirror 201. Because of the 45 degree angle and the compound surface of the mirror 201, the light can be reflected perpendicular to the longitudinal axis of the fiber 315 with a beam profile 213 that is close to circular when it exits the outer surface 217 of the lens 210.

Figure 1:
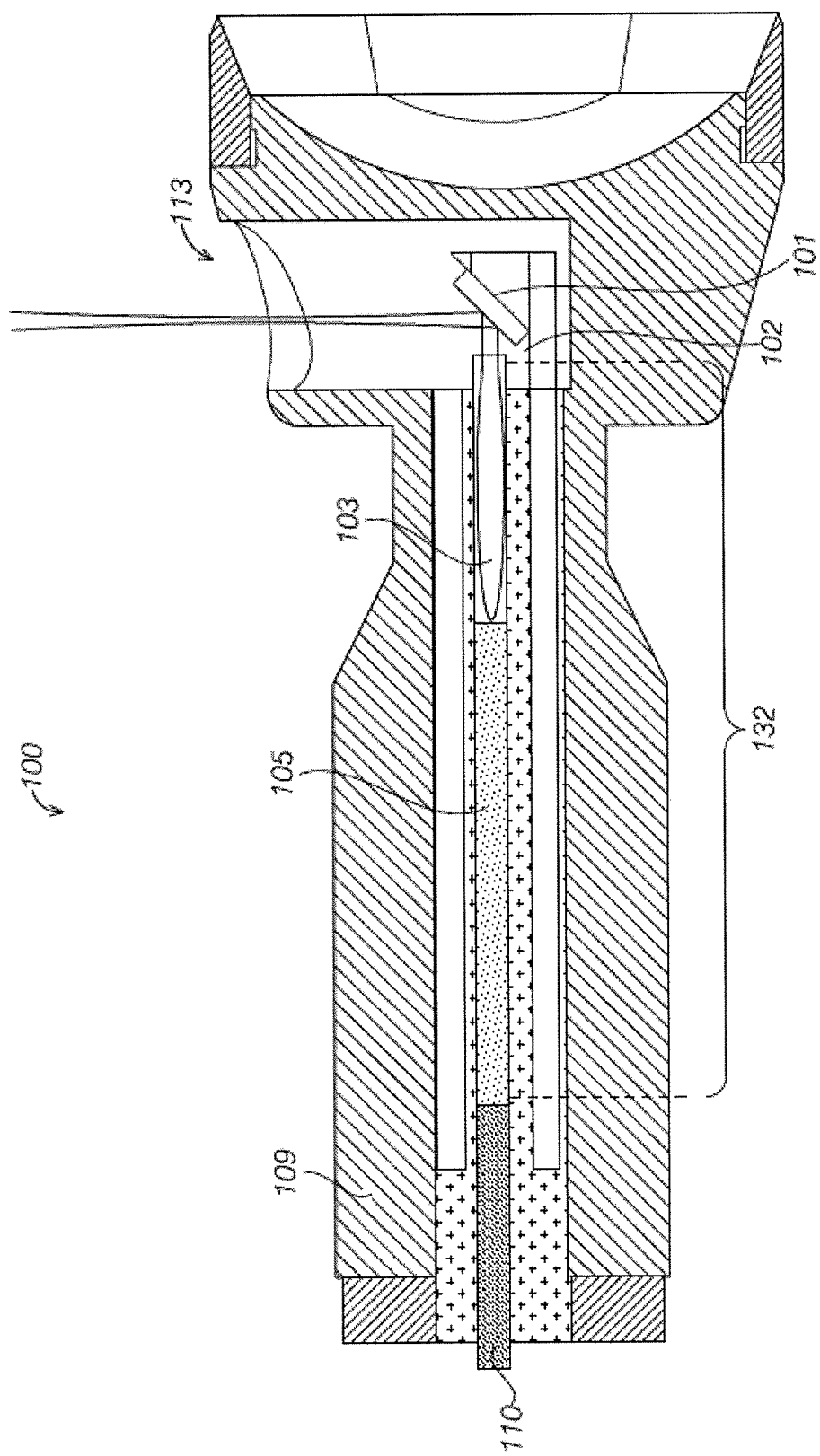
FIG. 1 is an example of a prior art apparatus including a separate lens (an optical fiber configured as a GRIN lens) coupled to the distal end of an optical fiber, embedded in epoxy into which a separate mirror element has also be embedded.

As shown in FIG. 2, the fiber 215 can include a stripped section 205 (i.e., a section that does not include a coating, such as a polyimide coating). In contrast to the prior art designs (e.g., device 100 of FIG. 1), the device 200 can include a much smaller fragile section that is made only of the stripped section 205 (i.e., it does not include a GRIN lens). Further, in contrast to the device 100, the device 200 can include a combined lens and reflecting element (i.e., both can be built into lens 210).

FIGS. 3A-3D illustrate another device 300 including an anamorphic lens 310. The lens 310 is similar to lens 210 except that the proximal surface 311 is lens is angled 2-20 degrees, such as greater than or equal to 8 degrees, relative to the distal end 311 of the optical fiber 315. The relative angle can be obtained by cleaving the distal end of the fiber at an angle and/or by cutting the proximal surface 311 at an angle. Because the surface 311 is angled relative to the distal end 311 of the optical fiber, the refractive indices of the interface medium 302 and the lens 310 can be chosen to be further apart from one another (i.e., can be greater than 0.01 or 0.02). The angle between the distal end of the optical fiber and the proximal surface 311 can ensure that only a minimal amount (e.g., less than −55 dB) of light will be reflected back from the surface 311 while allowing flexibility in the choice of interface medium (e.g., adhesive or epoxy) used to attach the lens 310 to the optical fiber 315.

Figure 3A:
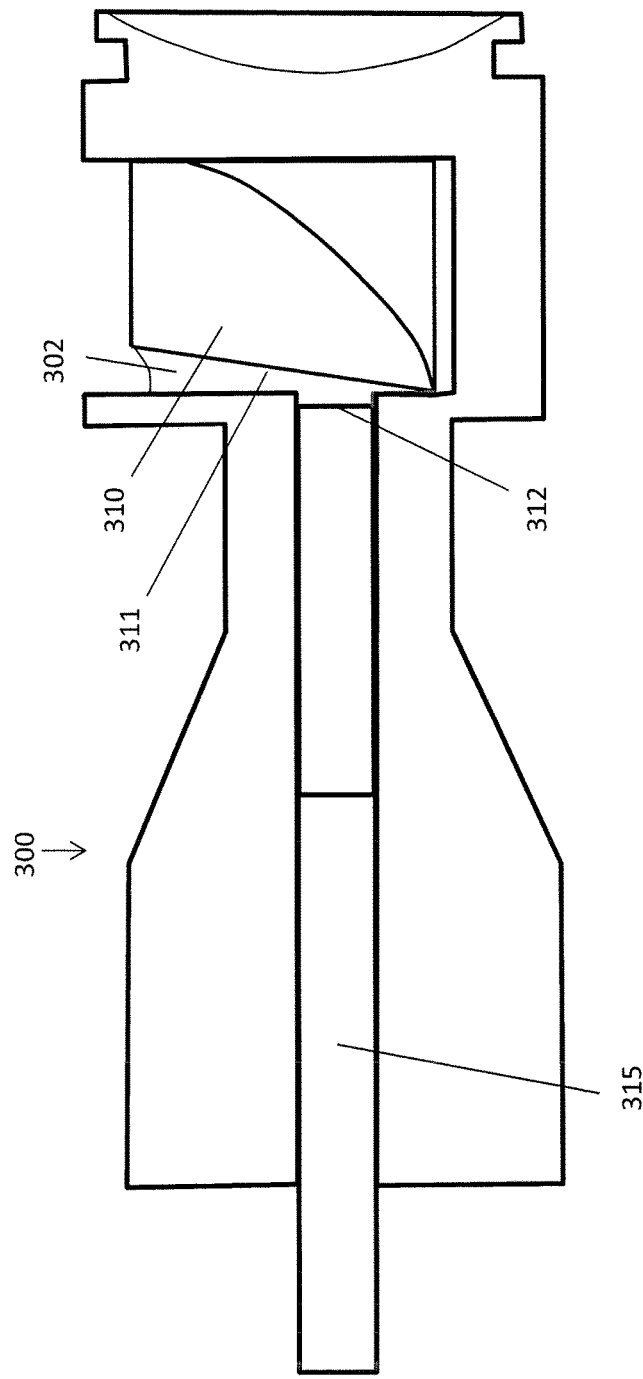
FIG. 3A is a schematic of a lens assembly within a portion of a catheter.
Figure 3B:
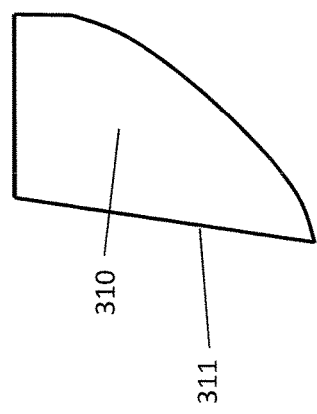
FIG. 3B shows a side sectional view through the lens of FIG. 3A.
Figure 3D:
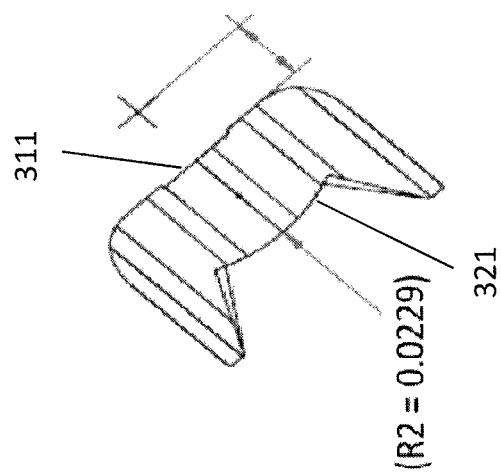
FIG. 3D shows a sectional view from the end of FIG. 3A.
Figure 3C:
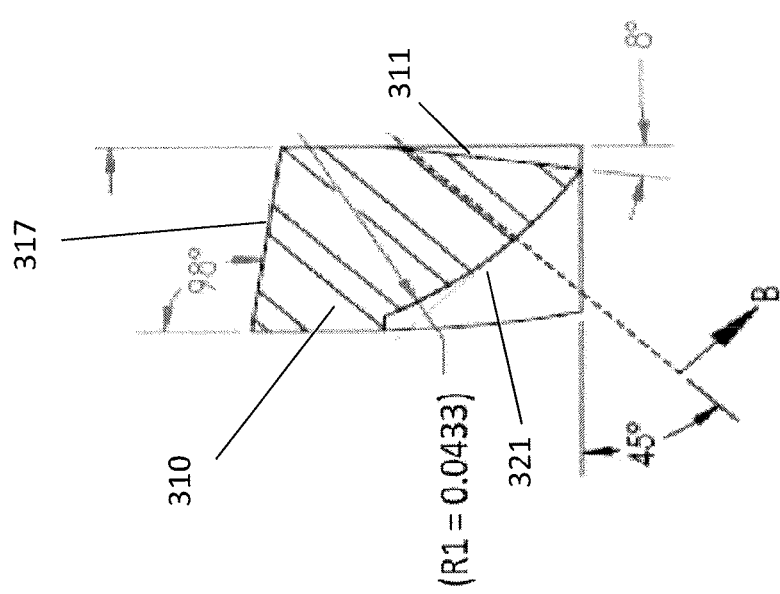
FIG. 3C shows a side sectional view from the opposite side as FIG. 3B.

Referring to FIGS. 3C-3D, in an exemplary embodiment of a lens 310, a first radius (R1) of the anamorphic lens can be 0.0433 inches while a second radius (R2) of the anamorphic lens can be 0.0229 inches. The angle of the proximal surface 311 can be 8 degrees relative to a distal end of the fiber while an angle of the outer surface 317 can be 8 degrees relative to an axis that is parallel with the longitudinal axis of the fiber. In another embodiment, R1 can be 0.0276 inches, and R2 can be 0.0269 inches, which can result in focusing the beam closer within the target. Further, as shown, the distal surface 321 can be angled at approximately 45 degrees relative to the longitudinal axis of the optical fiber (i.e., the angle between the optical axis and the tangent to the compound second surface at the intersection with the second surface).

Figure 4:
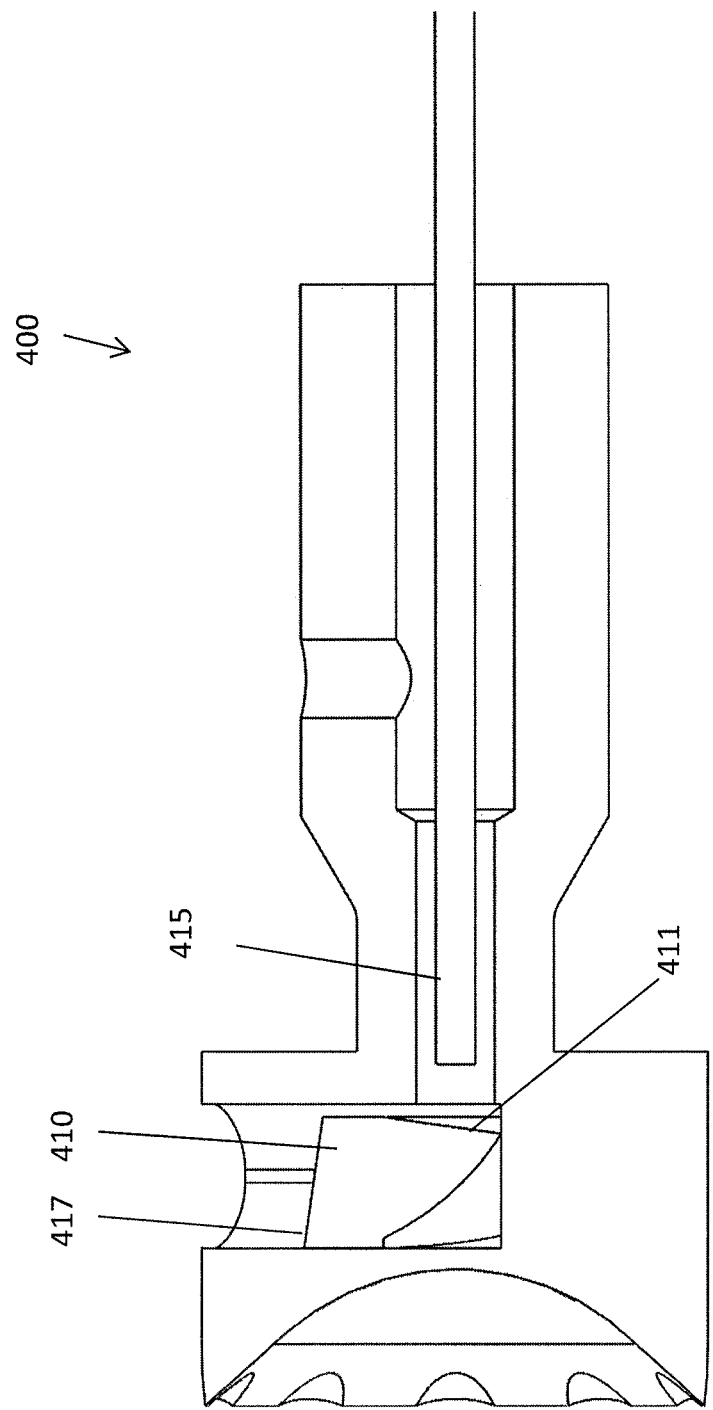
FIG. 4 shows another example of a catheter including a lens assembly as described herein.

FIG. 4 illustrates yet another device 400 including an anamorphic lens 410. The lens 410 is similar to lens 310 except that the outer surface 417 is angled relative to the longitudinal axis of the fiber. That is, the outer surface 417 can have an angle of between 2-20 degrees, such as 8 degrees or more, relative to an axis that is parallel to the axis of the fiber 417. Angling the surface 417 by 8 degrees or more advantageously ensures that a minimal secondary reflection is created by the surface 417 during imaging. In some embodiments, the surface 417 can be angled so as to make a 90 degree angle with the proximal surface 411. In other embodiments, the surface 417 can be angled in the opposite direction and/or can be angled by a different amount than the proximal surface 411 so as to prevent the formation of a 90 degree angle (thereby helping to prevent back-reflection into the optical fiber 415).

Figure 5B:
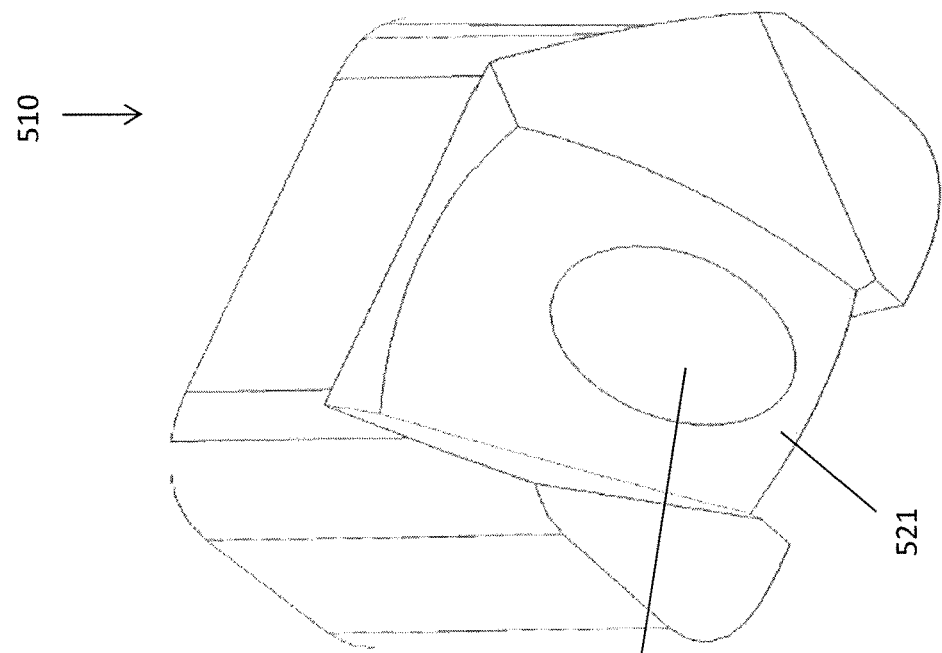
FIGS. 5A and 5B show perspective views of an exemplary lens assembly.
Figure 5A:
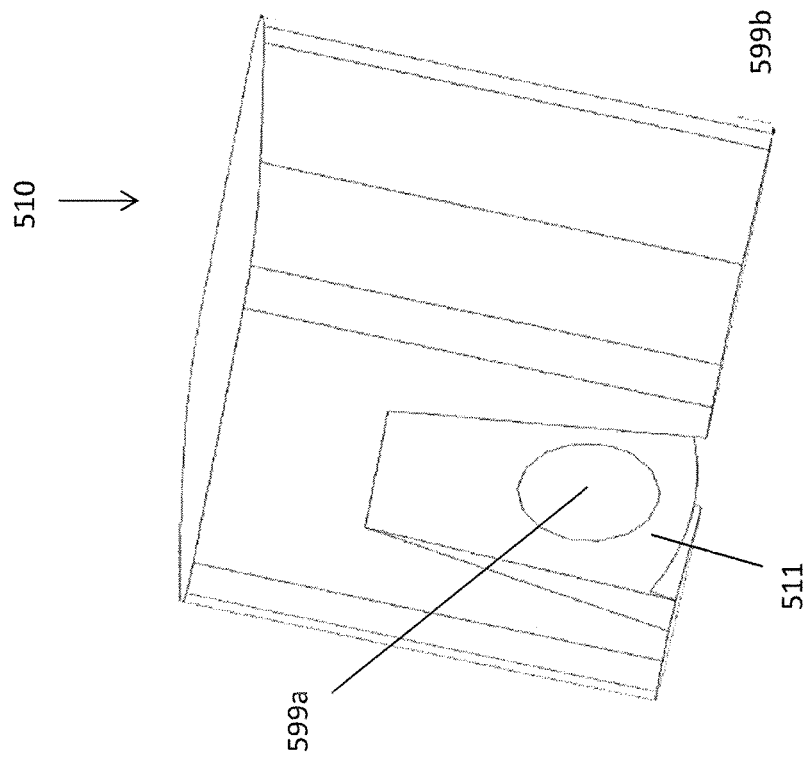

FIGS. 5A-5B show an embodiment of an anamorphic lens 510 similar to lens 410. In this embodiment, however, a circle 599a, 599b is drawn on each surface 521, 511, to show a focal area of each of the surfaces 521, 511. The circles 599a,b thus indicate the desired position of the beam when it hits the surfaces 521, 511. Ideally, the beam hits within circle 599b at an intersection of both optical axes (e.g., along R1 and R2). Further, the circles 599a,b can have a larger diameter than the diameter of the fiber to provide tolerance for placement of the fiber relative to the lens 510. For example, the circles 599a,b can have a diameter of 10-100 microns. The optical density and/or thickness of the coating can be configured so as to provide the desired reflections regardless of where the light beam is positioned within circle 599b. Accordingly, the placement of the optical fiber relative to the lens assembly 510 can be within a set tolerance, such as to allow movement within 50 microns of center of the circle 599b.

Figure 6A:
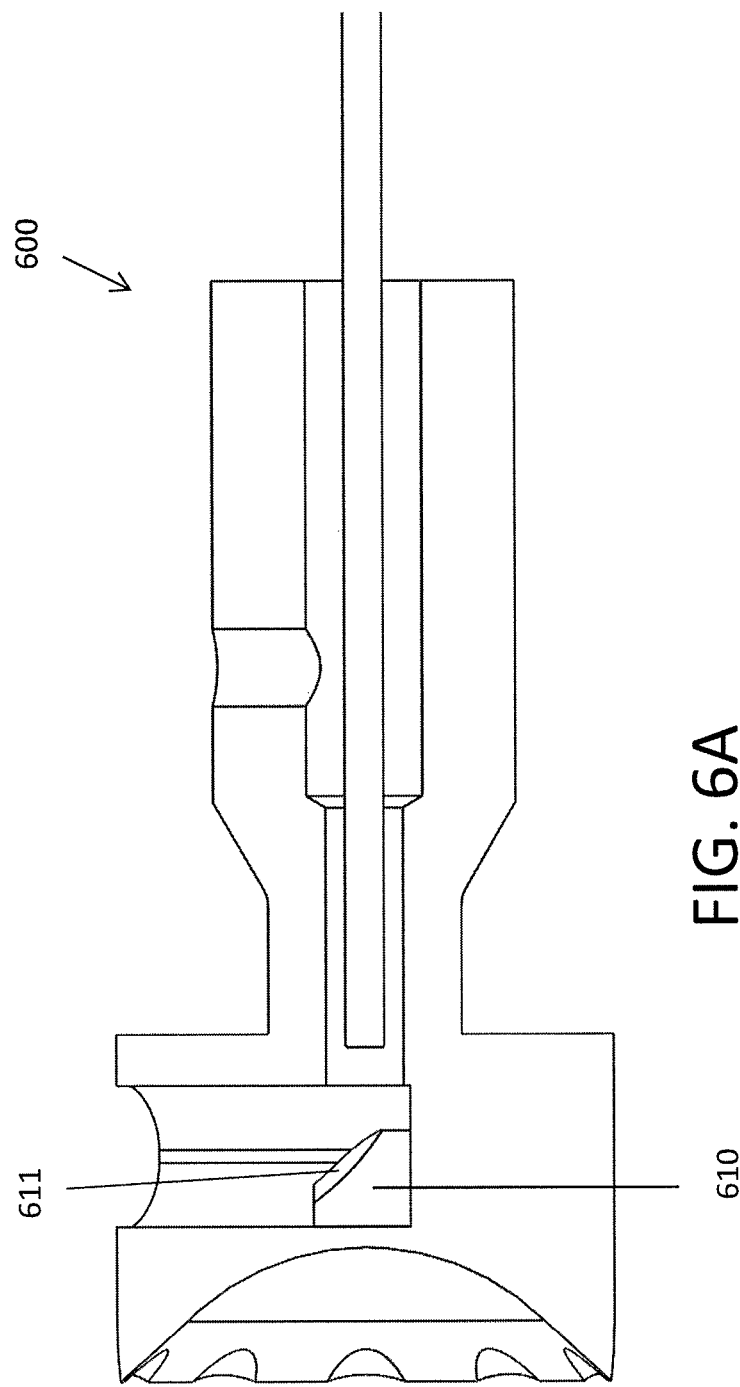
FIG. 6A shows another embodiment of a catheter including a lens assembly as described herein.
Figure 6C:
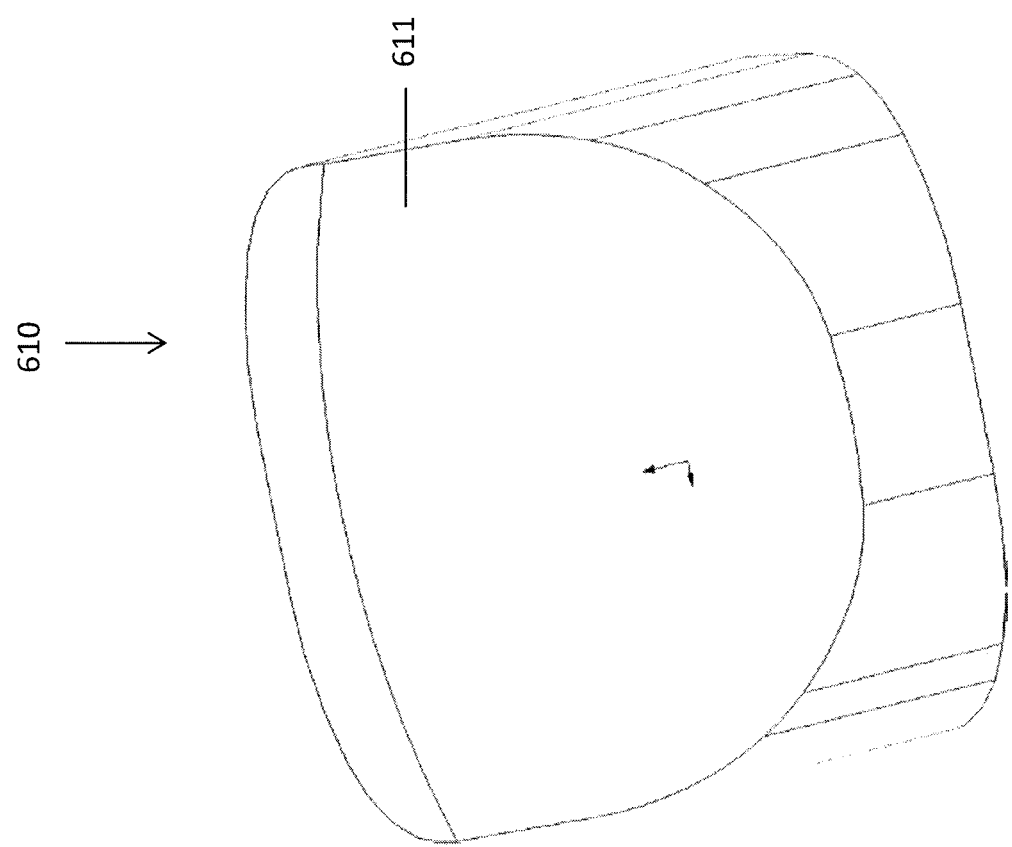
FIGS. 6B and 6C show perspective views of a lens assembly similar to that in FIG. 6A.
Figure 6B:
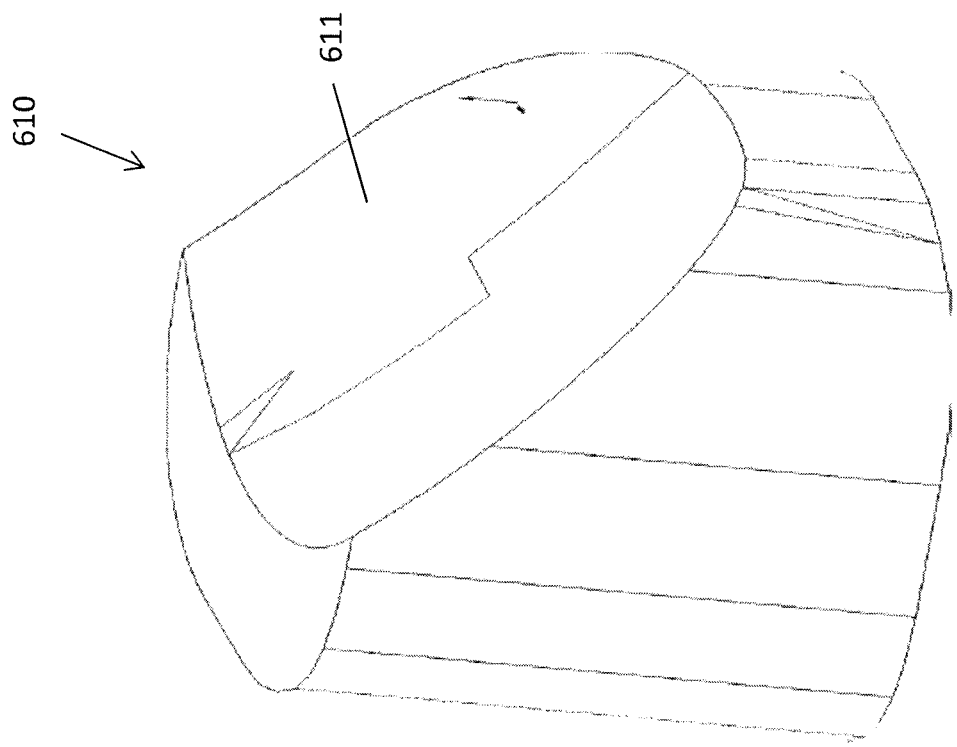

FIGS. 6A-6C illustrate another device 600 including an anamorphic lens 610. The lens 610 includes a proximal surface 611 that is both coated with a reflective coating, such as gold (as described above) and that has compound radii (i.e., is anamorphic). During use of this embodiment, the light thus does not travel through the lens, but instead immediately reflects off of the surface 611. The surface 611 can be concave and can have radii and/or a radius of curvature that are approximately the same as described above with respect to the distal surface 321.

Thus, as discussed above, the SMF-GRIN and mirror assembly required for many prior art devices can be replaced with a single anamorphic lens assembly as described herein.

In some embodiments, the anamorphic lenses described herein can be made of polycarbonate.

Further, in some embodiments, the lens assemblies described herein can be molded. Molding a material, such as a polycarbonate, can be relatively inexpensive and easy to make, simplifying the manufacturing process and lowering the cost for making imaging assemblies.

Figure 7A:
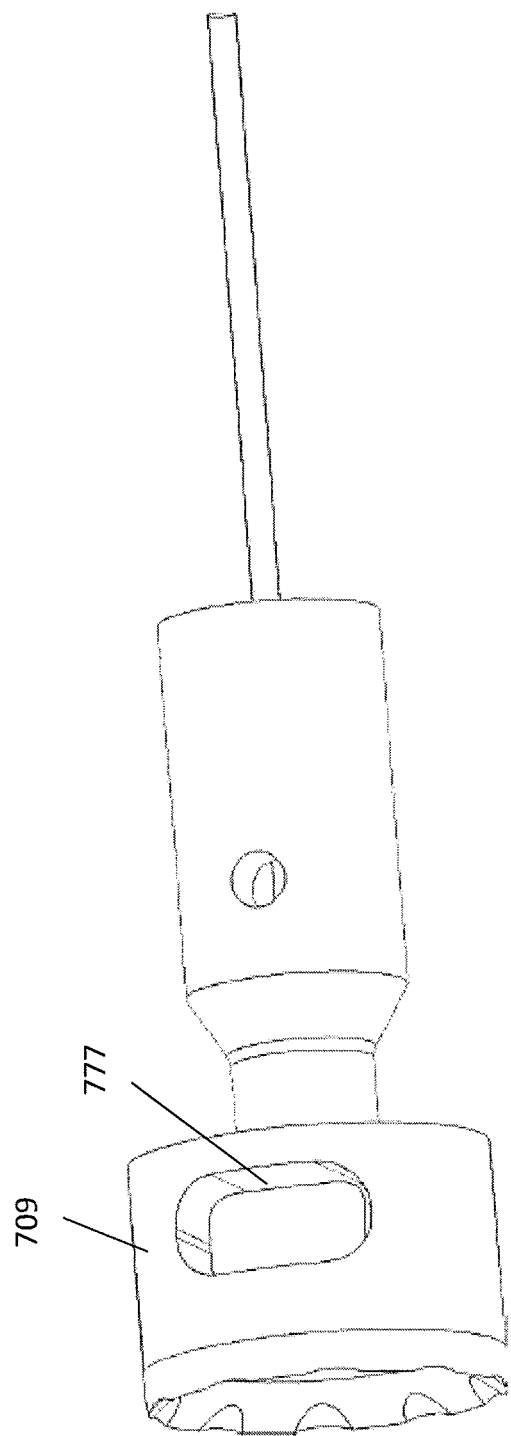
FIG. 7A shows an catheter with an exemplary pocket for placement of a lens assembly.
Figure 7B:
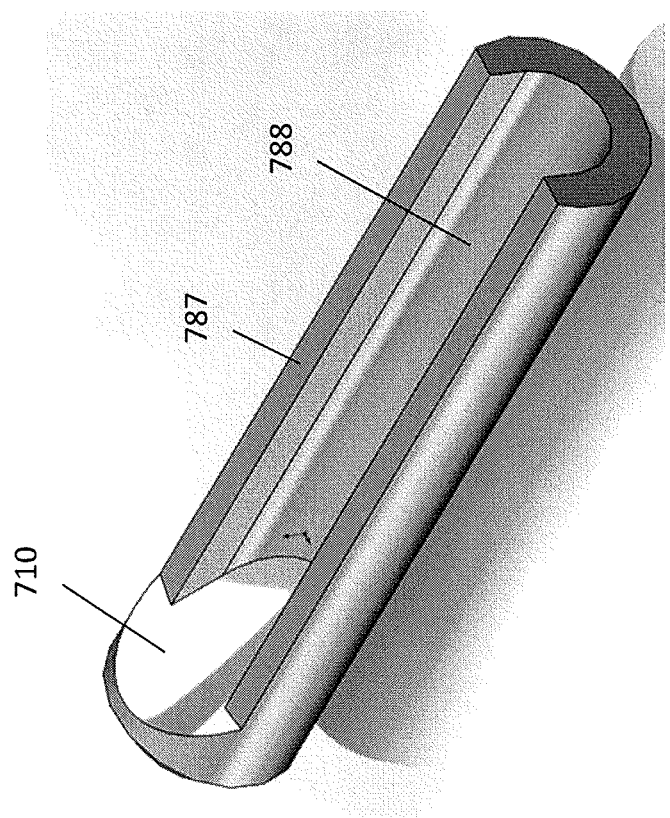
FIG. 7B shows a lens assembly built into a hypotube.

Referring to FIG. 7A, in some embodiments, the formed lens assembly can be dropped into a crevice 777 or hole in the device housing 709, and the hole can then be filled with the interface medium. Referring to FIG. 7B, in some embodiments, the formed lens assembly can be integral with a hypotube 787 having an elongate channel 788 extending therethrough. The optical fiber can then be placed within the channel 788 and the interface medium used to attach the fiber to the lens 710.

The interface mediums described herein can be, for example, an epoxy, such as a UV-curing epoxy.

As mentioned and illustrated, the use of the anamorphic lens assemblies described herein may shorten the length of the distal tip of the devices in which the assemblies are used. The length of the stripped section of the fiber may be much smaller, so the distal imaging and therapeutic housing can be made much smaller.

Figure 8:
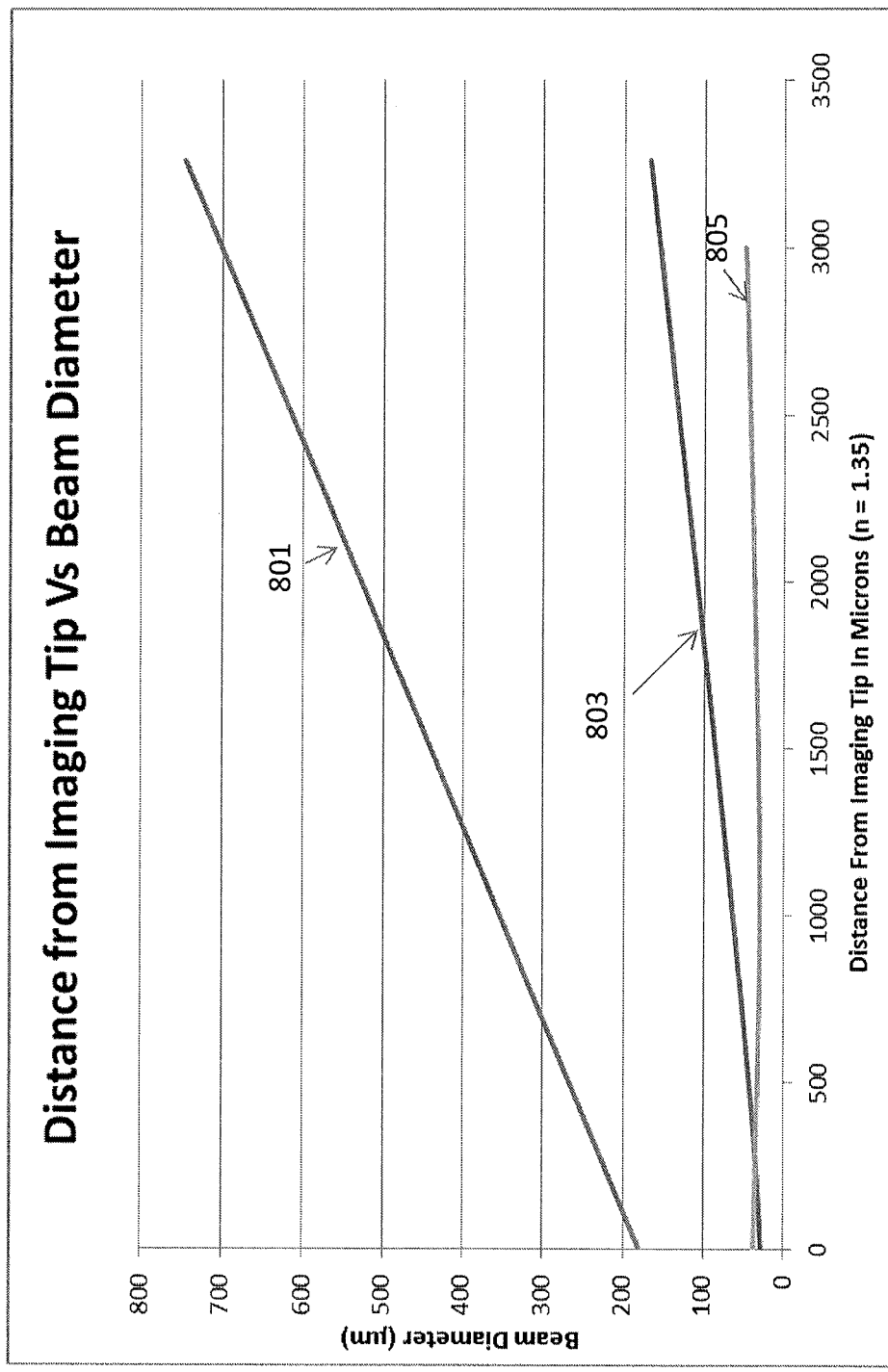
FIG. 8 is a graph illustrating the relative distances from the imaging tip versus beam diameter for each of a standard optical fiber, GRIN fiber and the improved lens apparatus as described herein, relative to beam diameter. As shown the beam diameter is much finer (smaller) for a much larger range of imaging tip distances, as compared to the prior art (GRIN) devices and devices without any lenses.

The lens assemblies described herein can have significantly better focusing capability suited to the geometry of a catheter. For example, the radius of curvature of the anamorphic lens structures described herein may be such that the focus is a preferred (further) distance away from the housing. FIG. 8 shows examples of a range of beam diameters relative to the distance from the imaging tip for an OCT catheter without a lens 801, with a GRIN fiber lens 803, and with the anamorphic lens apparatuses described herein 805. In this example, the beam diameter with 0 being the edge of the housing.

In some embodiments, the lens assemblies described herein can themselves cause the reflection of the light beam into the tissue. That is, the reflective surfaces can be uncoated, and the reflection can be caused by a total internal reflection resulting from the mismatch of the refractive indices between the lens material and the interface medium and/or air surrounding the lens. In such embodiments, the refractive index of the lens material can be high, such as 1.0 or greater, 1.2 or greater, 1.5 or greater, or 1.7 or greater. Further, in embodiments where light travels through the lens, the distal surface of the lens can be bordered by air to ensure total internal reflection.

In some embodiments, the reference reflection can be made by a surface other than the optical fiber/interface medium surface. For example, the reference reflection can be made by the proximal or distal surfaces of the lens assembly and/or by the outer surface of the lens assembly. In such an embodiment, the indices of refraction of the interface medium and the core of the optical fiber can be closely matched (e.g., within 0.02) in order to provide only minimal secondary reflection at that interface.

The lens assemblies described herein can be used with a variety of different imaging catheters. For example, the lens assemblies can be used with: U.S. patent application Ser. No. 12/829,277, filed Jul. 1, 2010, titled "ATHERECTOMY CATHETER WITH LATERALLY-DISPLACEABLE TIP," now U.S. Patent Application Publication No. 2011/0004107; U.S. patent application Ser. No. 12/829,267, filed Jul. 1, 2010, titled "CATHETER-BASED OFF-AXIS OPTICAL COHERENCE TOMOGRAPHY IMAGING SYSTEM," now U.S. Pat. No. 9,125,562; U.S. patent application Ser. No. 13/175,232, filed Jul. 1, 2011, titled "ATHERECTOMY CATHETERS WITH LONGITUDINALLY DISPLACEABLE DRIVE SHAFTS," now U.S. Pat. No. 9,345,510; U.S. patent application Ser. No. 13/433,049, filed Mar. 28, 2012, titled "OCCLUSION-CROSSING DEVICES, IMAGING, AND ATHERECTOMY DEVICES," now U.S. Pat. No. 8,644,913; U.S. patent application Ser. No. 14/401,175, filed Nov. 14, 2014, titled "ATHERECTOMY CATHETERS WITH IMAGING," now U.S. Patent Application Publication No. 2016/0141816; U.S. patent application Ser. No. 14/424,277, filed Feb. 26, 2015, titled "BALLOON ATHERECTOMY CATHETERS WITH IMAGING," now U.S. Patent Application Publication No. 2015/0208922; U.S. patent application Ser. No. 14/776,750, filed Sep. 15, 2015, titled "CHRONIC TOTAL OCCLUSION CROSSING DEVICES WITH IMAGING, now U.S. Patent Application Publication No. 2016/0029902; U.S. patent application Ser. No. 15/072,272, filed Mar. 16, 2016, titled "ATHERECTOMY CATHETERS DEVICES HAVING MULTI-CHANNEL BUSHINGS," now U.S. Patent Application Publication No. 2016/0192962; U.S. patent application Ser. No. 15/076,568, filed Feb. 5, 2016, titled "ATHERECTOMY CATHETERS AND OCCLUSION CROSSING DEVICES;" and International Patent Application No. PCT/US2015/039585, filed Jul. 8, 2015, titled "HIGH SPEED CHRONIC TOTAL OCCLUSION CROSSING DEVICES," now International Patent Publication No. WO 2016/007652, the entireties of which are incorporated by reference.

Figure 11:
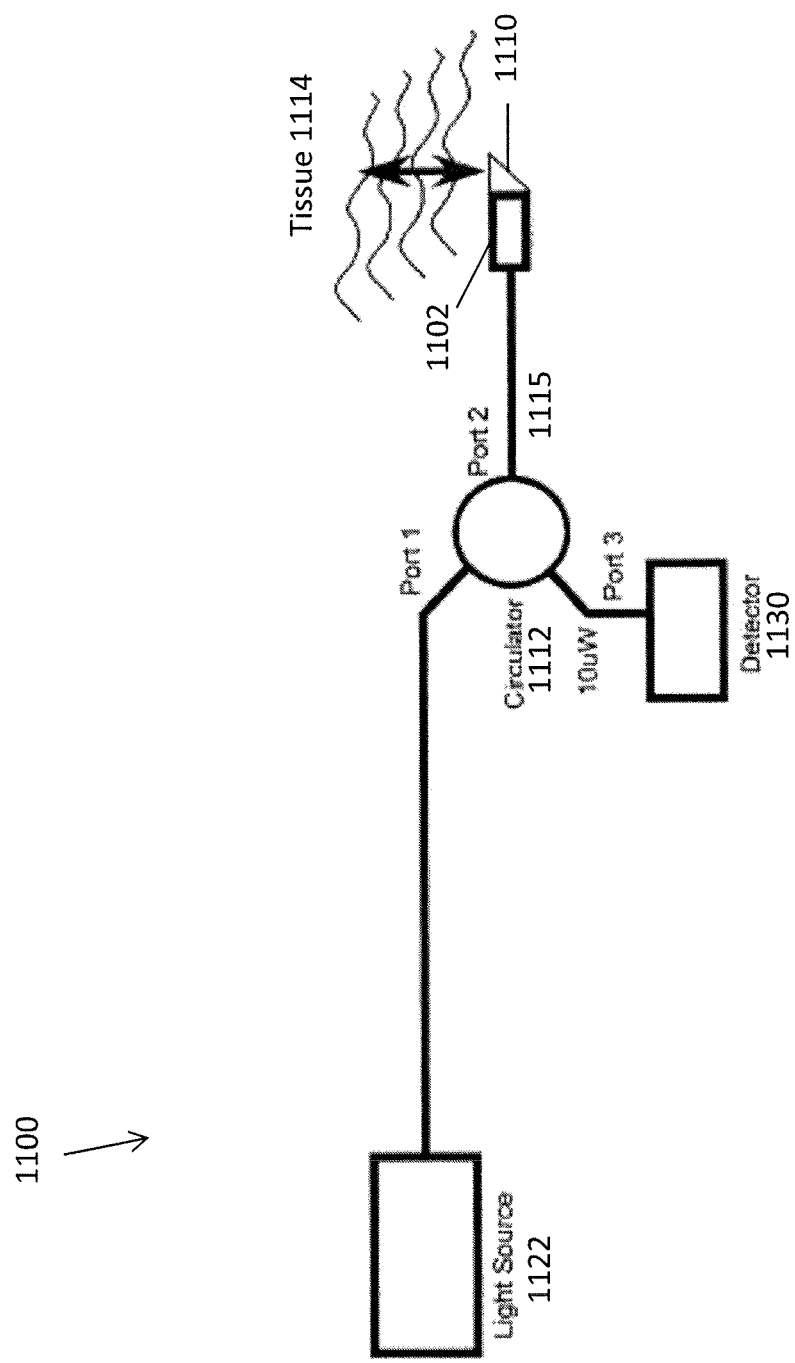
FIG. 11 shows an exemplary OCT system for use with a lens assembly as described herein.

The lens assemblies described herein can be used, for example, as part of an optical coherence tomography (OCT) system. Referring to FIG. 11, the system 1100 can therefore include a source of optical radiation 1122, a common path optical fiber 1115 (e.g., extending through a catheter elongate body), the lens assembly 1110, the interface medium or epoxy 1102, and a detector 1130 configured to receive the optical radiation reflected from the reference interface and the target 1114. The system 1100 can further include a processor to generate an image of the target based upon the optical radiation received by the receiving electronics. As is further shown in FIG. 11, a Faraday isolation device 1112, such as a Faraday Effect optical circulator, can be used to separate the paths of the outgoing light source signal and the target and reference signals returning from the distal end of the fiber. Exemplary OCT systems with which the lens assembly can be used are further described in U.S. patent application Ser. No. 14/400,140, filed on Nov. 10, 2014 (titled "OPTICAL COHERENCE TOMOGRAPHY WITH GRADED INDEX FIBER FOR BIOLOGICAL IMAGING"), the entirety of which is incorporated by reference herein.

In some embodiments, a secondary reflection of optical radiation from an interface between the optical fiber and the lens assembly is less than −60 dB. Further, in some embodiments, the reference interface provides a reference reflection of between −28 and −42 dB.

Also described herein are carbon dioxide supply cartridges that can be used, for example, to inflate a balloon of a balloon catheter.

Figure 9:
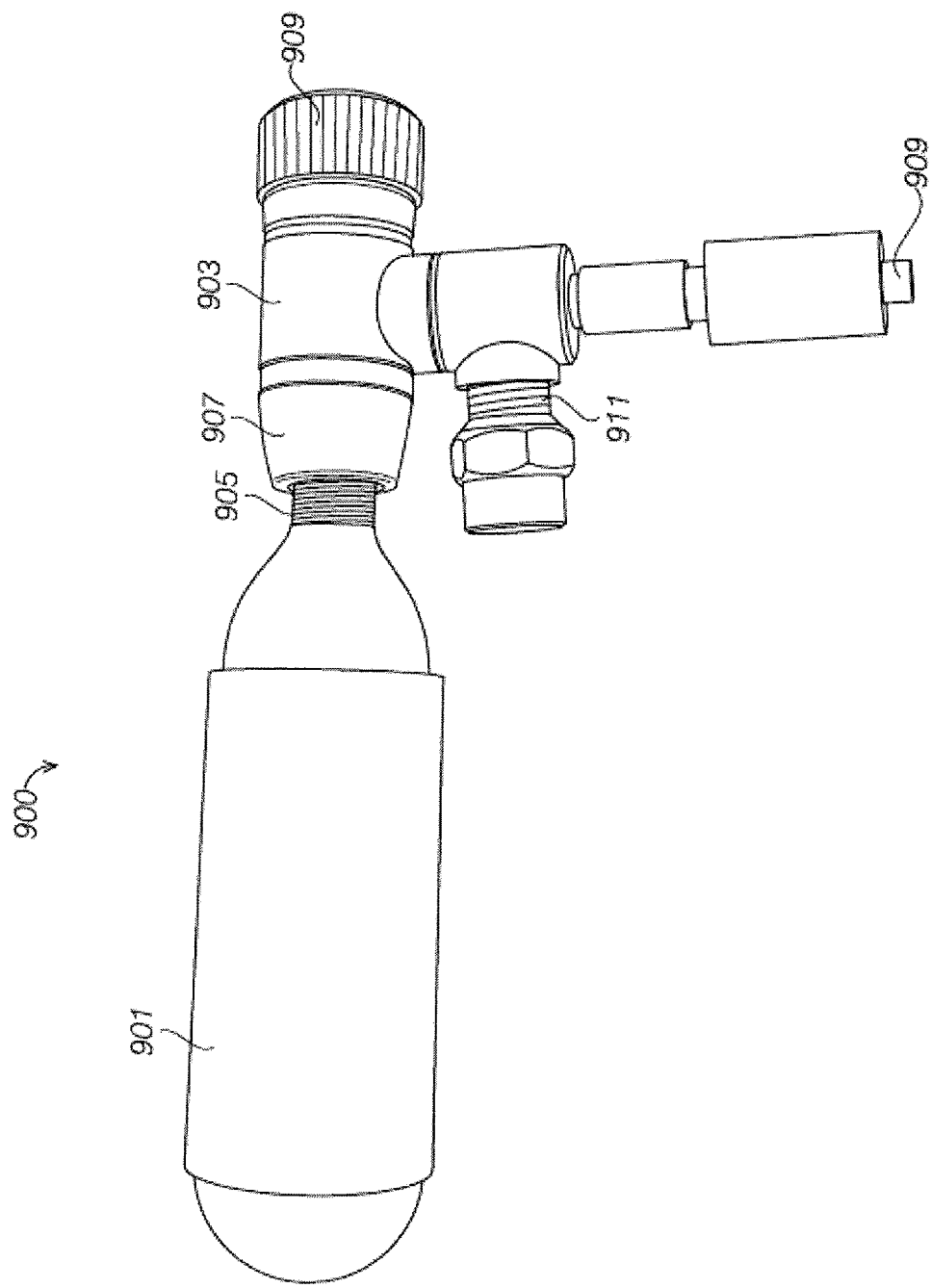
FIG. 9 shows an exemplary carbon dioxide cartridge.

FIG. 9 shows a single-use carbon dioxide supply cartridge or device 900. The device 900 includes a cylinder 901 filled with carbon dioxide and a valve assembly 903. In one embodiment, the cylinder 901 and the valve assembly 903 can be twisted relative to one another in order to open the cylinder and pressure the valve assembly 903. For example, the cylinder 901 can have a threaded male portion 905 while the valve assembly 903 can include a threaded female portion 907. The valve assembly 903 can further include a piercing element, such as a needle, configured to break a seal on the cylinder 901 when the threaded portions 905, 907 are connected together. The valve assembly 903 can further include a rotational valve 919 configured to control or restrict flow of the gas therethrough. Further, a check valve 911 can be configured to control the maximum inflation pressure. For example, the check valve 911 can limit the inflation pressure to 15 psi. A catheter connection 909 can mechanically connect to the catheter and provide a flow path for the carbon dioxide from the device 900 to the balloon.

Figure 10:
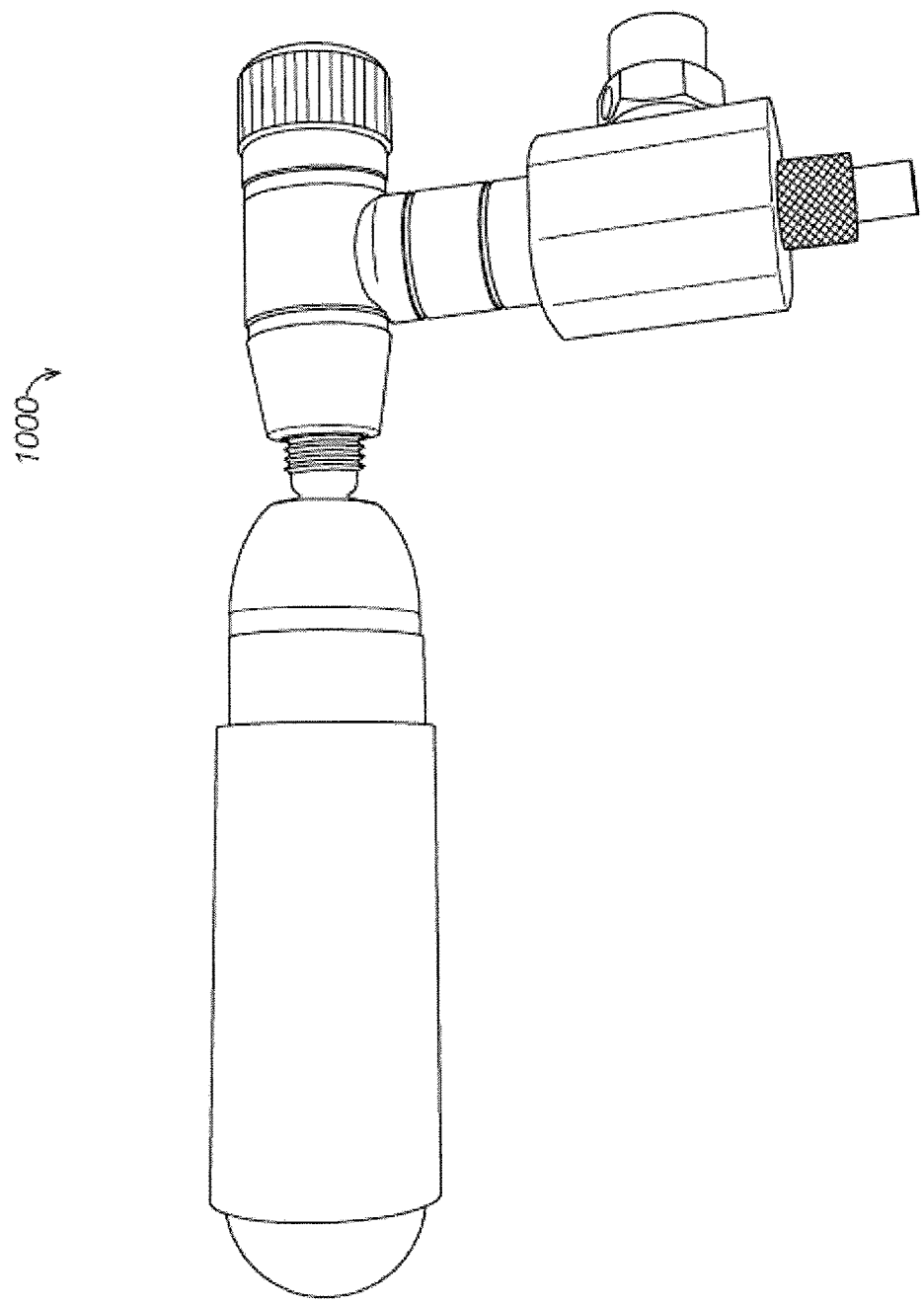
FIG. 10 shows another embodiment of an exemplary carbon dioxide cartridge.

FIG. 10 shows another embodiment of a single-use carbon dioxide supply device 1000 with similar features as device 900.

The carbon dioxide supply devices 900, 1000 can be used with a variety of different balloon catheters. For example, the devices 900, 1000 can be used with balloon atherectomy catheters, such as those described in International Patent Application No. PCT/US2013/032494, filed Mar. 15, 2013, titled "BALLOON ATHERECTOMY CATHETERS WITH IMAGING," and International Patent Application No. PCT/US2015/014613, filed Feb. 5, 2015, titled "ATHERECTOMY CATHETERS AND OCCLUSION CROSSING DEVICES," incorporated by reference herein in their entireties. The carbon dioxide supply device 100 can further be used, for example, with balloon angioplasty catheters. Advantageously, the carbon dioxide supply devices 900, 1000 can be a single-use sterile product.

Although described as a carbon dioxide supply, other inflation gases can be used in devices 900, 1000.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A catheter for optical coherence tomography (OCT), comprising:
    an elongate catheter body extending distally to proximally;
    an optical fiber in the elongate catheter body; and
    a lens assembly comprising a lens body having a concave proximal surface that is opposite from and at an angle relative to the distal end of the optical fiber, the lens body attached to and optically coupled with a distal end of the optical fiber by an interface medium;
    wherein the proximal surface has a compound radius having a first radius along a first axis that is different from a second radius along a second axis;
    wherein the proximal surface comprises a reflective material configured so that at least 90% of a light reaching the lens body from the distal end of the optical fiber reflects off of the proximal surface; and
    wherein the optical fiber and the lens assembly are together configured to provide a common path for optical radiation reflected from a target and from a reference interface formed between the distal end of the optical fiber and the interface medium.

2. The catheter system of claim 1, wherein the interface medium is an epoxy.

3. The catheter system of claim 1, wherein a tangent of the proximal surface is at an angle of between about 40 degrees and 50 degrees relative to a longitudinal axis of the fiber.

4. The catheter system of claim 1, wherein the reflective material comprises a reflective coating on the proximal surface.

5. The catheter system of claim 4, wherein the reflective coating comprises gold.

6. The catheter system of claim 4, wherein the reflective material comprises dielectric.

7. The catheter system of claim 4, wherein the reflective coating has an optical density of greater than 3.0.

8. The catheter system of claim 1, wherein the lens body comprises a polycarbonate material.

9. The catheter system of claim 1, wherein a secondary reflection of optical radiation from an interface between the optical fiber and the lens assembly is less than −60 dB.

10. The catheter system of claim 1, wherein the reference interface provides a reference reflection of between −28 and −42 dB.

11. The catheter system of claim 1, wherein a radius of curvature of the proximal surface is between 0.2 mm and 1.5 mm.

12. The catheter system of claim 1, further comprising a source of optical radiation configured to provide the light, wherein a reflective coating on the proximal surface has a thickness of at least ⅙ of an excitation wavelength of the source of optical radiation.

13. The catheter system of claim 1, further comprising a source of optical radiation, receiving electronics configured to receive optical radiation reflected from the reference interface and the target, and a processor to generate an image of the target based upon the optical radiation received by the receiving electronics.

* * * * *